United States Patent [19]

Paradis

[11] Patent Number: 5,699,821
[45] Date of Patent: Dec. 23, 1997

[54] CONTROL OF FLUID FLOW

[76] Inventor: Joseph R. Paradis, P.O. Box 22238, Hltn Hd Is., S.C. 29925

[21] Appl. No.: 290,136

[22] Filed: Aug. 15, 1994

Related U.S. Application Data

[63] Continuation-in-part of Ser. No. 135,673, Oct. 13, 1993, Pat. No. 5,509,433.

[51] Int. Cl.$^6$ ........................................ A61M 5/00
[52] U.S. Cl. .................. 137/1; 251/149.1; 251/149.8; 604/167; 604/256
[58] Field of Search .................... 251/149.8, 149.6, 251/149.1; 604/83, 256, 283, 905, 167, 249; 137/903, 1

[56] References Cited

U.S. PATENT DOCUMENTS

| | | | |
|---|---|---|---|
| 3,831,629 | 8/1974 | Mackal et al. | 137/903 X |
| 4,429,856 | 2/1984 | Jackson . | |
| 4,512,766 | 4/1985 | Vailancourt . | |
| 4,915,687 | 4/1990 | Sivert . | |
| 5,006,114 | 4/1991 | Rogers et al. . | |
| 5,064,416 | 11/1991 | Newgard et al. . | |
| 5,085,645 | 2/1992 | Purdy et al. . | |
| 5,147,333 | 9/1992 | Raines . | |
| 5,203,775 | 4/1993 | Frank et al. | 604/283 X |
| 5,242,393 | 9/1993 | Brimhall et al. | 604/283 X |
| 5,269,771 | 12/1993 | Thomas et al. | 251/149.1 X |
| 5,273,533 | 12/1993 | Bonaldo . | |
| 5,300,034 | 4/1994 | Behnke et al. . | |
| 5,306,243 | 4/1994 | Bonaldo . | |
| 5,354,275 | 10/1994 | Behnke et al. . | |
| 5,380,306 | 1/1995 | Brinon . | |
| 5,470,319 | 11/1995 | Mayer | 604/167 |
| 5,474,536 | 12/1995 | Bonaldo . | |
| 5,487,728 | 1/1996 | Vaillancourt . | |
| 5,549,577 | 8/1996 | Siegel et al. . | |

FOREIGN PATENT DOCUMENTS

| | | |
|---|---|---|
| 0309771 | 9/1988 | European Pat. Off. . |
| 9311828 | 6/1993 | WIPO . |

*Primary Examiner*—Kevin Lee

[57] ABSTRACT

A flow control device with an inlet for fluid and a normally open slotted movable member sealing the inlet and closing the slot. The unsealing of the inlet and the opening of the slot permits the passage of fluid therethrough. The movable member extends by a channel, which can be open or closed, between the inlet and an outlet and has a portion which is expandable laterally. A member external to the flow control device, such as the tip of a Luer taper, can activate the movable member by depressing it to open the slot and allow the flow of fluid.

20 Claims, 19 Drawing Sheets

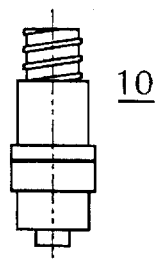
FIG. 3A
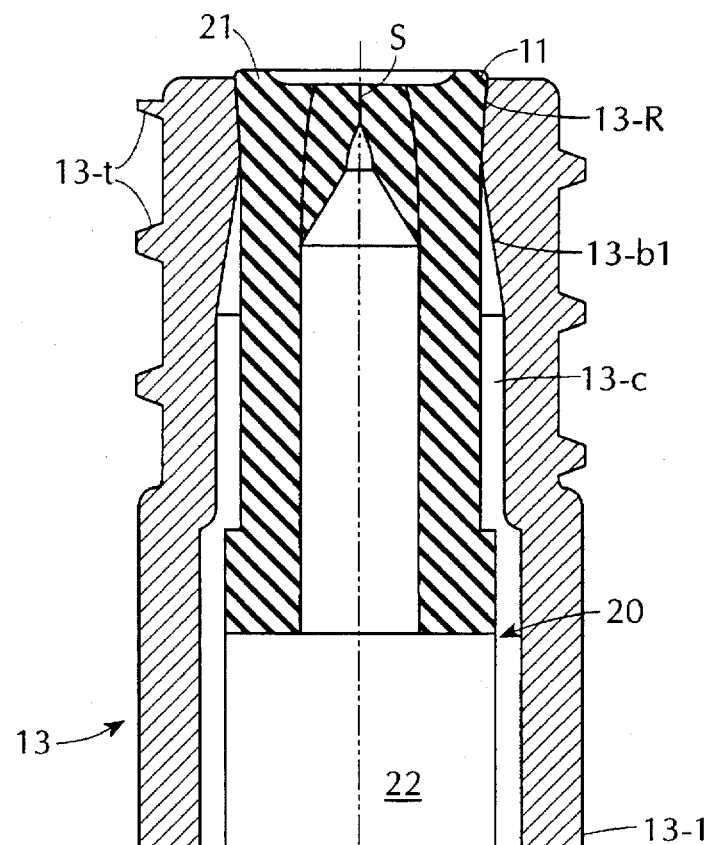
FIG. 3B
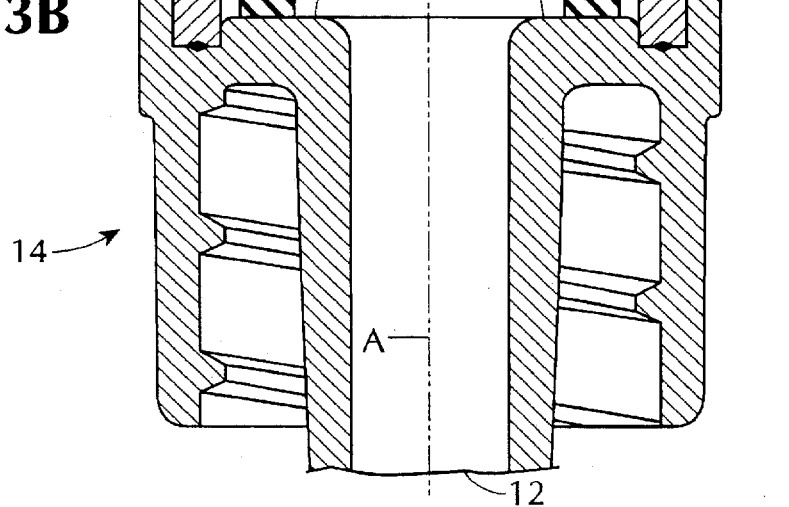

CONTROL OF FLUID FLOW

BACKGROUND OF THE INVENTION

This is a continuation-in-part of Ser. No. 08/135,673 filed Oct. 13, 1993, U.S. Pat. No. 5,509,433. The invention relates to flow control and more particularly, to the control of fluid flow with respect to the infusion and aspiration of fluids in venous and arterial systems.

A common container for medical fluids is a plastic pouch which contains saline, i.e. a salt solution used in investigation of biological and physiological processes. The contents of such a container are carried by a conduit, typically plastic tubing, through a "check" valve that is used to prevent backflow.

In addition, other check valves can be used with the conduit to provide for the infusion and/or aspiration of other substances, such as medicaments, body fluids, and anesthetics. Infusion is commonly used to introduce saline or other medical fluids into veins, while aspiration is commonly used to draw fluids from body cavities.

The ordinary check valve used with conduits from medicinal containers functions by the deflection of an elastomeric element towards and away from a valve seat. The deflection is towards the valve seat in order to prevent flow, and away from the seat to permit flow.

In some cases the control of fluid flow is with respect to a multiplicity of channels that have varying degrees of convergence with one another. A typical multichannel arrangement makes use of connectors which permit the intercoupling of flow channels. For example, when two channels are to be joined to permit a common output, the connector can take the form of a fitting that resembles a "Y". When one of the channels terminates in an infusion site, the prior practice has been to access the site by needles, which are undesirable.

Because of the desirability of achieving needleless injection and infusion of fluids, one effort has resulted in Rogers et al. U.S. Pat. No. 5,006,114 of Apr. 9, 1991 in which a valve assembly has a Luer lock on an inlet, and movable piston seals the inlet.

When a syringe is attached to the Rogers inlet the piston is displaced to unseal a fluid channel which connects the end of the syringe to an outlet, and then to a device connected to a patient. When the syringe is removed from the inlet the piston is moved to its original closed position by an internal spring of the valve. This device suffers from the disadvantage that the requirement of a spring for acting against the piston results in a force against the inserted Luer tip that increases as the piston is displaced.

In addition, the Rogers medical valve assembly provides an outlet channel that is displaced at an angle in relation to the inlet. As a consequence of this angular displacement, it is difficult to manufacture the device since there is a tendency for flash to accumulate at the entrance of the outlet channel in the vicinity of the piston. In addition, the angular configuration of the Rogers valve does not lend itself to manifold application.

Moreover, the Rogers design is intended for a Luer fitting which does not have a taper so that when the conventional tapered Luer fitting is employed, it can become jammed in the straight line walls of the inlet.

An attempt to overcome the disadvantages of Rogers is disclosed in Raines, U.S. Pat. No. 5,147,333, which issued Sep. 15, 1992. In the Raines patent there is accommodation for a tapered Luer fitting, but there is the continued disadvantage of the necessity for using a spring to urge a piston or spool forwardly during closure of the valve and rearwardly when the valve is being opened.

As a result, the disadvantageous increase in spring force with displacement continues to be present. Furthermore, the Raines "backcheck" valve requires a pair of vertically offset ports that extend laterally from a tubular body and the spool or piston is disposed between the ports. In addition, like the predecessor Rogers valve the piston or spool in Raines requires at least one projection from the end of the piston contacted by a Luer tip in order to permit the flow of fluid from the Luer tip through the valve.

Furthermore, like the Rogers predecessor, the Raines valve is subject to difficulties in manufacture because of flash since the various outlet ports are angularly, i.e., perpendicularly, oriented in relation to their inlets.

Accordingly, it is an object of the invention to achieve needleless injection, infusion and aspiration without the need for spring-loaded members, such as pistons or spools where the counterforce exerted by the spring increases as the piston is displaced. A related object of the invention is to overcome the disadvantages characterizing the needleless injection valves of Rogers, U.S. Pat. No. 5,006,114 and Raines, U.S. Pat. No. 5,147,333.

A further object of the invention is to overcome the need for angular orientation of an outlet in relation to an inlet in order to avoid manufacturing difficulties such as the creation of flash which can clog or reduce the volume of fluid flow from an inlet to an outlet.

Yet another object of the invention is to permit the non-use of projections on a closure for an inlet, whereby a Luer fitting can open an inlet channel without the need for engaging one or more projections on a closure.

Other arrangements are disclosed in Newgard, U.S. Pat. No. 5,064,416; Sivert, U.S. Pat. No. 4,915,687 and Jackson, U.S. Pat. No. 4,429,856. These arrangements are complex and difficult to manufacture with numerous disadvantages.

Another objection to existing arrangements is that their activators are not interchangeable. Thus injection sites that require needle injection cannot be used without needles; conversely injection sites that are externally actuated by inserting a member that opens a diaphragm cannot be used with needles. In addition, the non-needle injection sites present problems of sterility. In order to have external access to the control diaphragm, it is necessary to have an open channel that can become contaminated. Even when a temporary seal is provided for the open channel, removal of the seal prior to injection allows inadvertent contamination. This is by contrast with an injection site having a needle-puncturable surface. The latter can be wiped clean with a sterilizing agent before injection is to take place.

A further object of the invention to enhance the control that can be achieved over fluid flow. A related object is to enhance flow control where fluid infusion or combination is to take place.

An important object of the invention is to eliminate the need for needle usage at injection sites, while permitting needle usage if that is desired. A related object is to maintain sterility at injection sites that are operated without needles, while simultaneously permitting such sites to be used with needles if necessary.

An additional object of the invention is to improve the performance of valves for infusion, injection, aspiration and control of fluid flow.

A further object of the invention is to achieve tamper-evident arrangements for components used in the infusion and aspiration of medicinal fluids.

SUMMARY OF THE INVENTION

In accomplishing the foregoing and related objects the invention provides a flow control device with an inlet for the flow of fluid, an outlet connected to the inlet and disposed to serve as a conduit for flow into the inlet and a movable member having a normally open slotted and compressible head for sealing the inlet. The movable member also has a flexible body which can include a closed channel and extends to the outlet for permitting flow through the head to the outlet when the inlet is unsealed.

In accordance with one aspect of the invention, the inlet extends to a tapered bore which is spaced from the movable member, and the slot of the head is opened when the head is moved to the tapered bore. The tapered bore can extend to a second bore within which the flexible body is expandable laterally with respect to the axis of the outlet. The flexible body can be rectangular in cross-section and spaced from the second bore.

In accordance with another aspect of the invention, activation of the movable member can be accomplished externally to the flow control device, for example, by the tip of a Luer taper which seals on the top surface of the head as it depresses the head of the movable member in order to allow the opening of the slot and unseal the inlet.

In accordance with a further aspect of the invention, a closed channel member extends into the outlet and is movable therein. The flexible body can include the closed channel member and a spring, of metal or plastic, for biasing, so that the removal of a force causing the closed channel member to move into the outlet causes the closed channel member to return to its equilibrium position.

The head may include outwardly tapered and slotted side walls so that the taper of the head promotes the sealing of the inlet and the slotted side walls facilitate the movement of the head to its sealing position.

The slot of the head advantageously is in the form of a multi-sided geometric figure with opened segments when the head is in a non-sealing position. At the entrance to the inlet, the head may also have a depressed surface that is complementary to the tip of a Luer taper.

In a method of controlling fluid flow in accordance with the invention, the steps include (1) sealing an inlet by a slotted flexible stopper which contracts as it moves into the tapered inlet and closes the aperture of the stopper; and (2) depressing the stopper to allow the slot to open and permit the flow of fluid therethrough. The stopper can be depressed by applying the tip of a Luer taper which can seal a circumferential area on top of the stopper. The depression of the stopper allows its expansion and opens its slot to permit the throughpassage of fluid.

The method of the invention further includes wiping the side wall of the region into which the stopper is expanded during its depression, and following the return of the stopper to its equilibrium position. The method can further include the step of causing fluid to flow through a closed channel to an outlet, and the closed channel can be caused to move into the outlet. The closed channel can be spring loaded, by a suitably resilient material, to cause the return of the head to its equilibrium position when pressure is removed.

In a method of fabricating a flow control device, the steps include (a) molding a rectangular inlet member having an axis of flow, an inlet, a coaxial seat beyond the inlet, and an expansion chamber beyond the coaxial seat; (b) molding a rectangular outlet member which complements the inlet member and has a rectangular coaxial support; (c) inserting an apertured, expandable and rectangular control member into the inlet member; and (e) joining the outlet member to the inlet member with the expandable control member against the outlet support.

The control member can be molded of an elastomeric material with opposed legs, and can include an inner cylindrical shell for sealing to the extended outlet wall.

DESCRIPTION OF THE DRAWINGS

FIG. 3A is a scale view of the other side of the flow-control valve of FIG. 1A in accordance with the invention;

FIG. 3B is an enlarged sectional view of the flow-control valve of FIG. 3A in its closed valve position;

FIGS. 10A through 10E are end views of alternative tips for plugs in accordance with the invention;

DETAILED DESCRIPTION

Figures 1A, 1B:
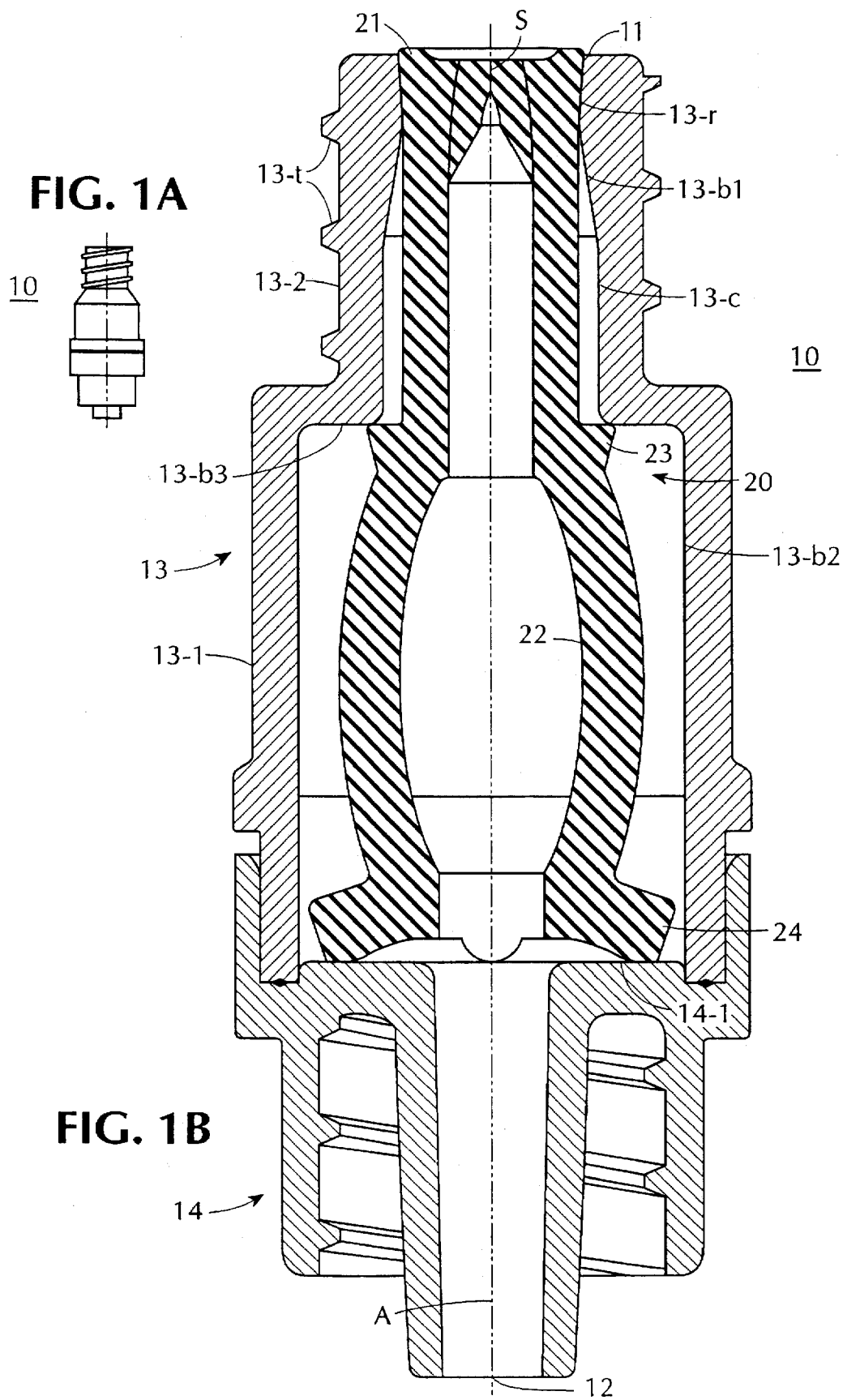
FIG. 1A is a scale view of one side of a flow-control valve in accordance with the invention.
FIG. 1B is an enlarged sectional view of the flow-control valve of FIG. 1A in its closed valve position.

With reference to the drawings, FIGS. 1A and 3A are scale views of different sides of a flow-control valve 10 in accordance with the invention. The valve 10 is rectangular in cross-section having the specific configuration described in detail below, with FIG. 1A showing the longer side and FIG. 3A showing the shorter side.

In FIG. 1B, which is an enlarged sectional view, the flow-control valve of FIG. 1A is shown in its "pre-loaded" condition with its inlet 11 sealed by the head 21 of a depressible plug 20. As indicated in FIG. 1B, the head 21 of the plug 20 has a closed slot S. In addition, the valve 10 has an outlet 12 connected to the inlet 11 and disposed to serve as a conduit for the throughflow of fluid that is applied at the inlet 11, through the slot S.

Figure 2A:
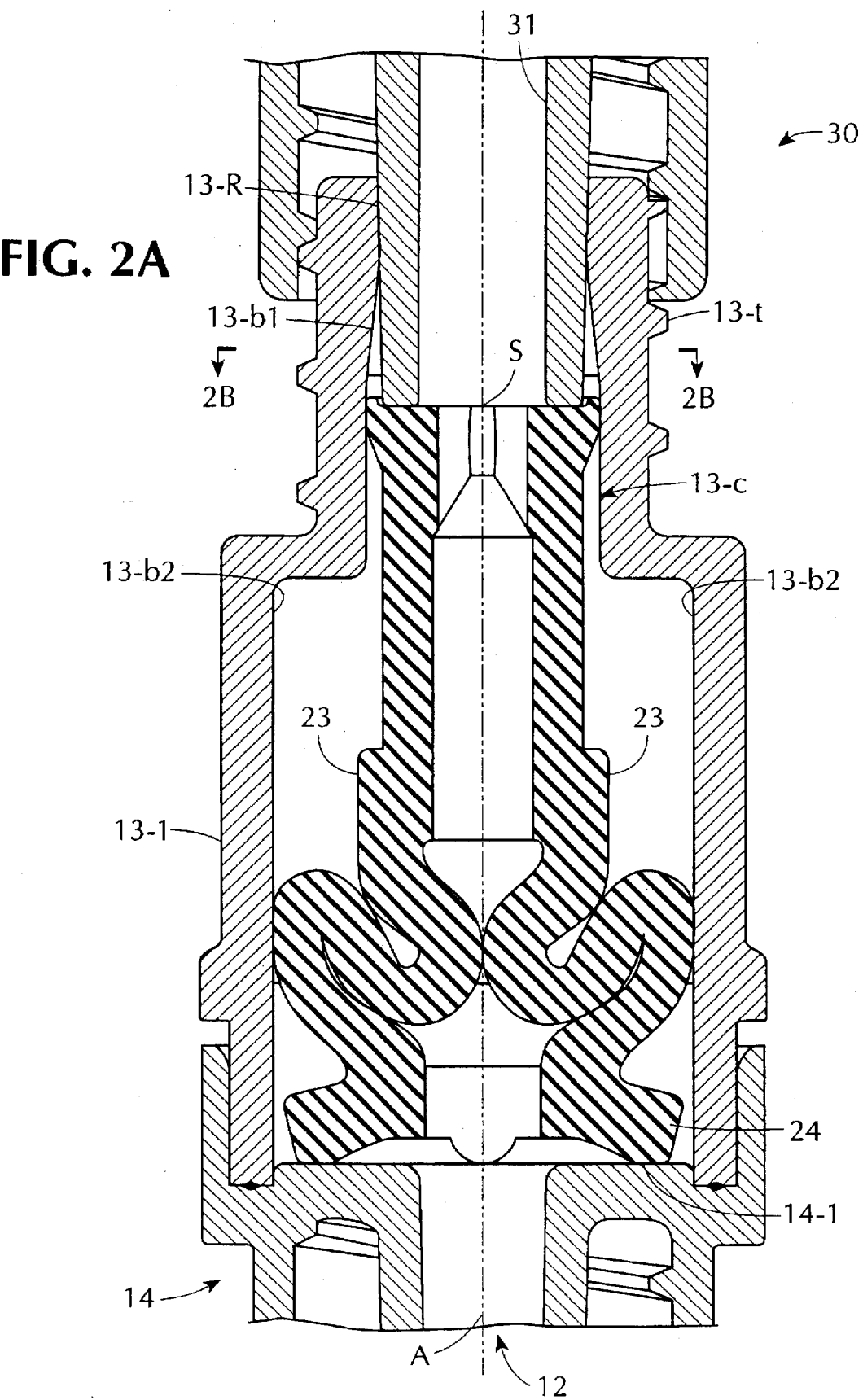
FIG. 2A is an enlarged sectional view of the flow-control valve of FIG. 1A in its "operational flow" position with an external pressure member.

The depressible plug or movable member 20 (as shown further in FIGS. 5A through 6E) has a flexible head 21 which seals the inlet 11 and extends to a flexible body 22 for controlling flow by the outward flexing of the body 22 when the head 21 is depressed as indicated in FIG. 2A.

In effect, the plug 20 forms a bell-shaped member with a hollow head 21 and a slotted body 22. The base of the body 22 terminates in a circumferential rectangular base 24. The rectangularity avoids twisitng during compression.

In the flow control device 10, the movable plug 20, together with the head 21 and the flexible body 22, extends between the inlet 11 and the outlet 12. The flexible body 22 is expandable laterally with respect to the vertical axis A of the outlet channel 12 in order to create spring pressure during opening and closing of slot S. Consequently the upper housing 13 has an enlarged expansion chamber 13-1. In addition, the housing 13 has a neck 13-2 with exterior Luer threads 13-t and an inwardly tapered bore 13-b1 beyond an interior cylindrical rim 13-r. Extending from the inwardly tapered bore 13-b1 is a cylindrical bore 13-c which, in turn, extends to a rectangular walls 13-b2. The latter extends to the expansion chamber 13-1.

A shoulder 23 of the plug 20 engages the horizontal wall 13-b3 proximate the bore 13-c of the expansion chamber 13-1. The head 21 seals the inlet 11 by being compressed against the inwardly tapered bore 13-b1, and cylindrical rim 13-r as described below. The head 21 remains in sealing contact with the tapered bore 13-b1 of the neck 13-2, and then with the bore 13-c, as the plug is depressed.

Figure 2B:
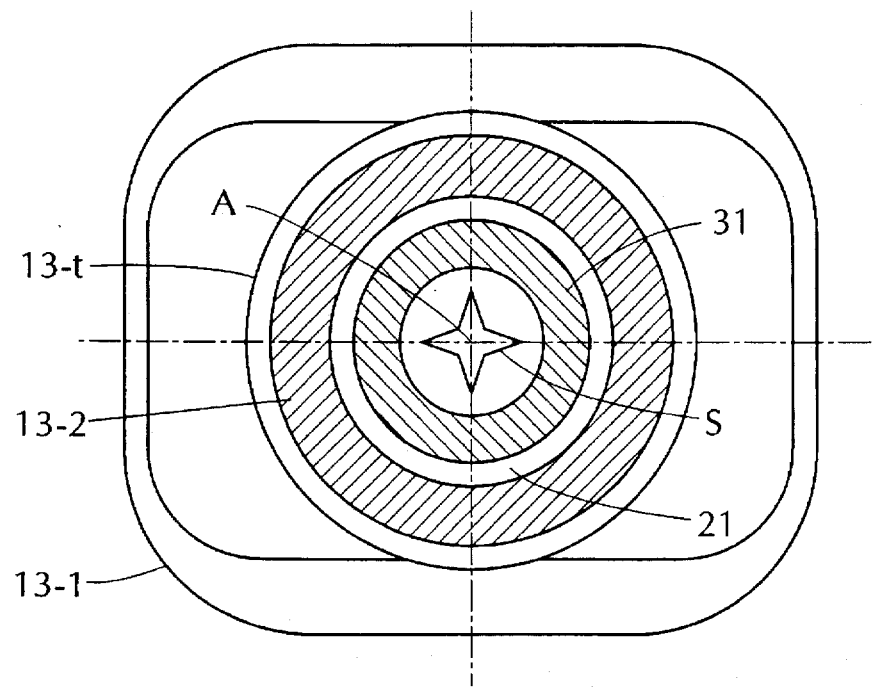
FIG. 2B is a sectional view of the flow-control valve of FIG. 2A taken along the lines 2B—2B.
Figure 4A:
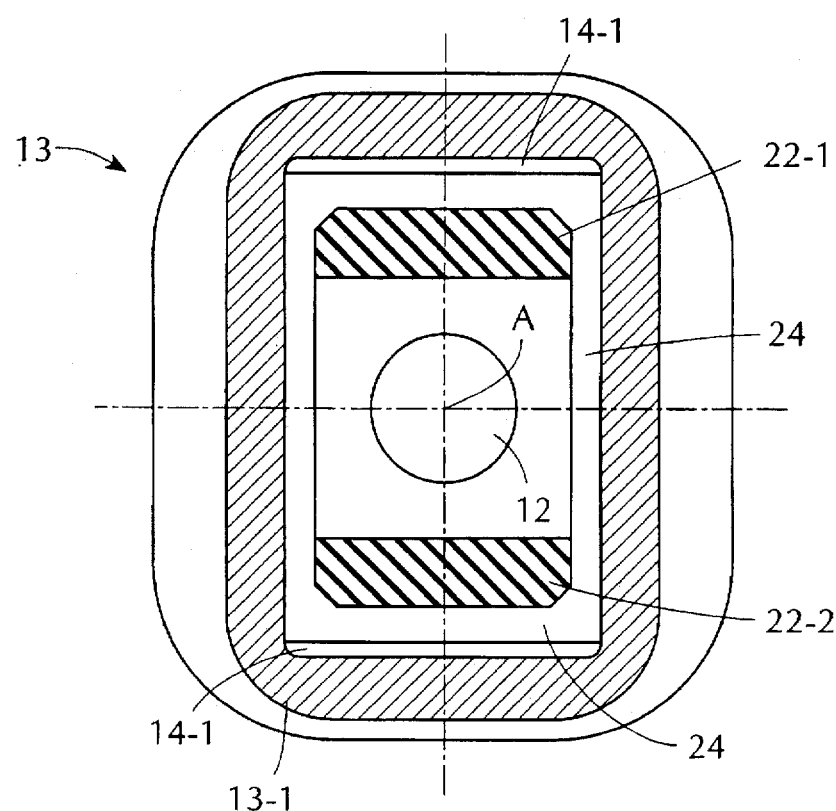
FIG. 4A is a sectional view of the flow-control valve of FIG. 3A taken along the lines 4A—4A.

However, when the bore 13-c at the end of the tapered bore 13-b1 is reached the slot S opens as shown in FIGS. 2A and 2B. Within the expansion chamber 13-1 the two legs of the body 22 can be spaced from the rectangular walls as shown in FIG. 4A.

For the embodiment of FIGS. 1B, 2A and 3B, the head 21 of the plug 20 has an upper slot 21-s so that when a Luer tip, such as the tip 31 of FIG. 2A is threaded on the neck 13-2 it seals circumferentially on top of plug 20 and there is no impediment to flow from the interior of the tip 31. This embodiment is particularly useful for relative low pressure infusion of fluids, e.g. by gravity flow from a saline bag (not shown). It is to be noted that because of the slot 21-s, pressure against the outer surface of the head 21 does not cause a collapse of material which could block the tip 31.

The Luer tip 31 thus permits activation of the control plug by a member external to the flow control device 10 since the plug 20 is seated in the inlet 11 and can be depressed from its compressed seal position to the bore 13-c. In effect the control is by a bell-shaped member with its upper portion sealing the inlet, and walls straddling the outlet. The walls are extended legs 22-1 and 22-2 which are bowed under pressure in the axial direction of the outlet channel 12. The slotted walls 22-1 and 22-2 are flexed or buckled under pressure. They extend from the head 21 sealing the inlet 11 to a base 14-1 of a lower body 14 encircling the outlet channel 12.

Figure 2C:
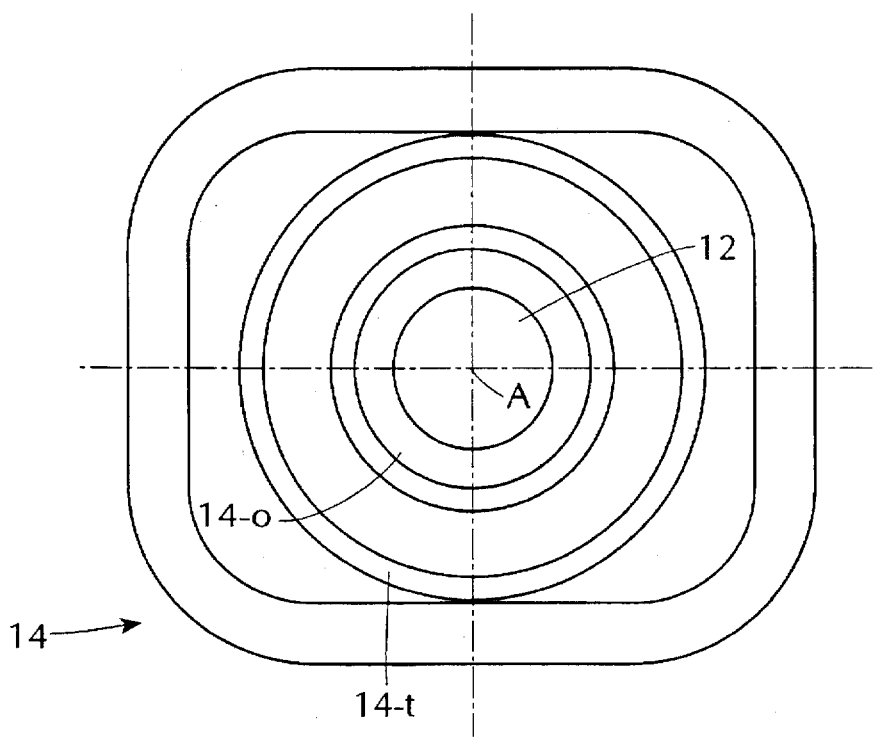
FIG. 2C is a bottom view of the flow-control valve of FIG. 2A.
Figure 4B:
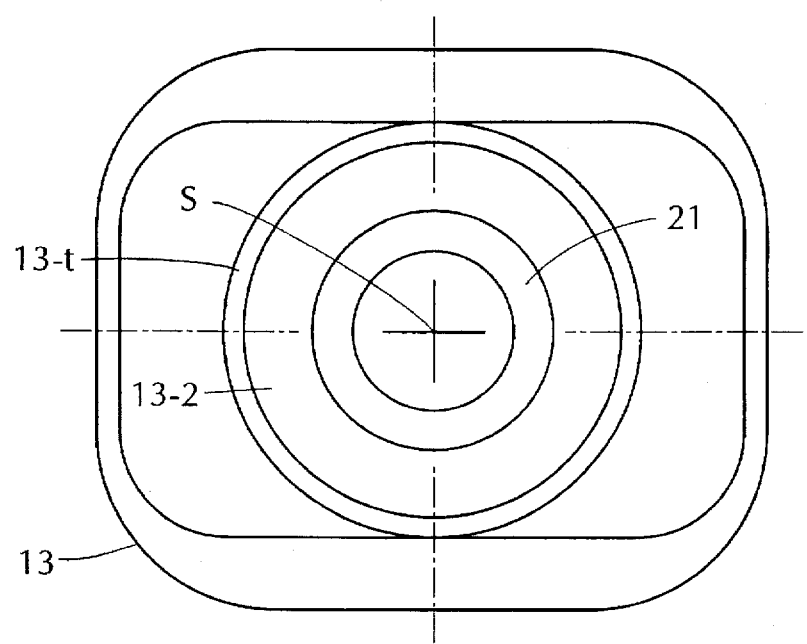
FIG. 4B is a top view of the flow-control valve of FIG. 3A.

FIG. 2B is a sectional view of the flow-control valve of FIG. 2A taken along the lines 2B—2B, while FIG. 2C is a bottom view of the flow-control valve of FIG. 2A. FIG. 3B is an enlarged sectional view of the flow-control valve of FIG. 3A in its "closed" condition, while FIG. 4A is a sectional view of the flow-control valve of FIG. 3A taken along the lines 4A—4A, and FIG. 4B is a top view of the flow-control valve of FIG. 3A.

The component elements 13 and 14 are locked together by snap action, but can be joined, for example, by ultrasonic welding. The valves of the invention promote sterility by providing ease of accessibility. Prior art valves with recessed stoppers allow antimicrobial agents to accumulate in puddles on the tops of stoppers. Particulate matter may also collect on recessed tops.

Figures 5A, 5B:
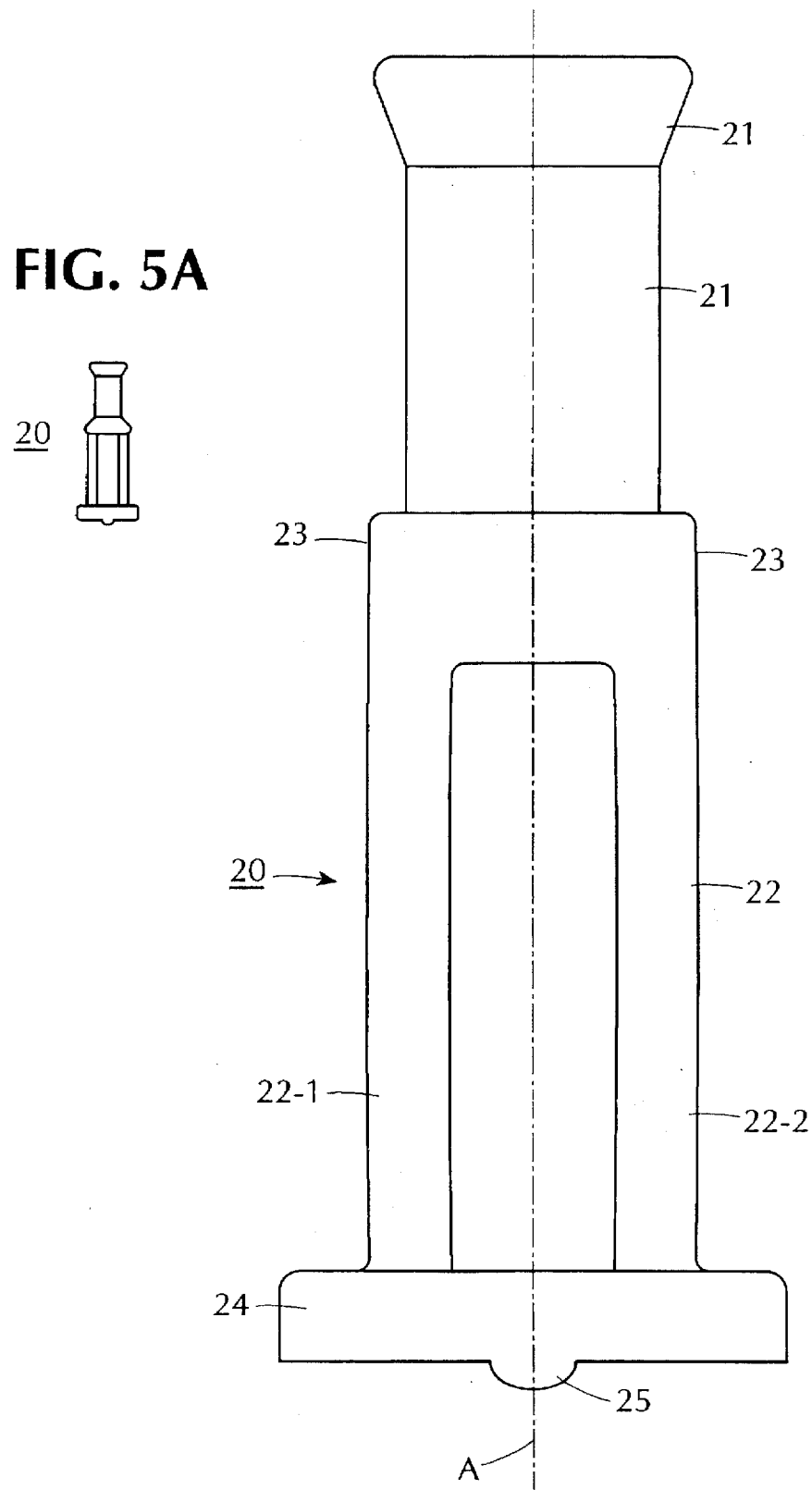
FIG. 5A is a scale view of one side of a flow-control plug for the valve of FIG. 1A.
FIG. 5B is an enlarged view of the flow-control plug of FIG. 5A in its "pre-installation" condition.
Figure 5C:
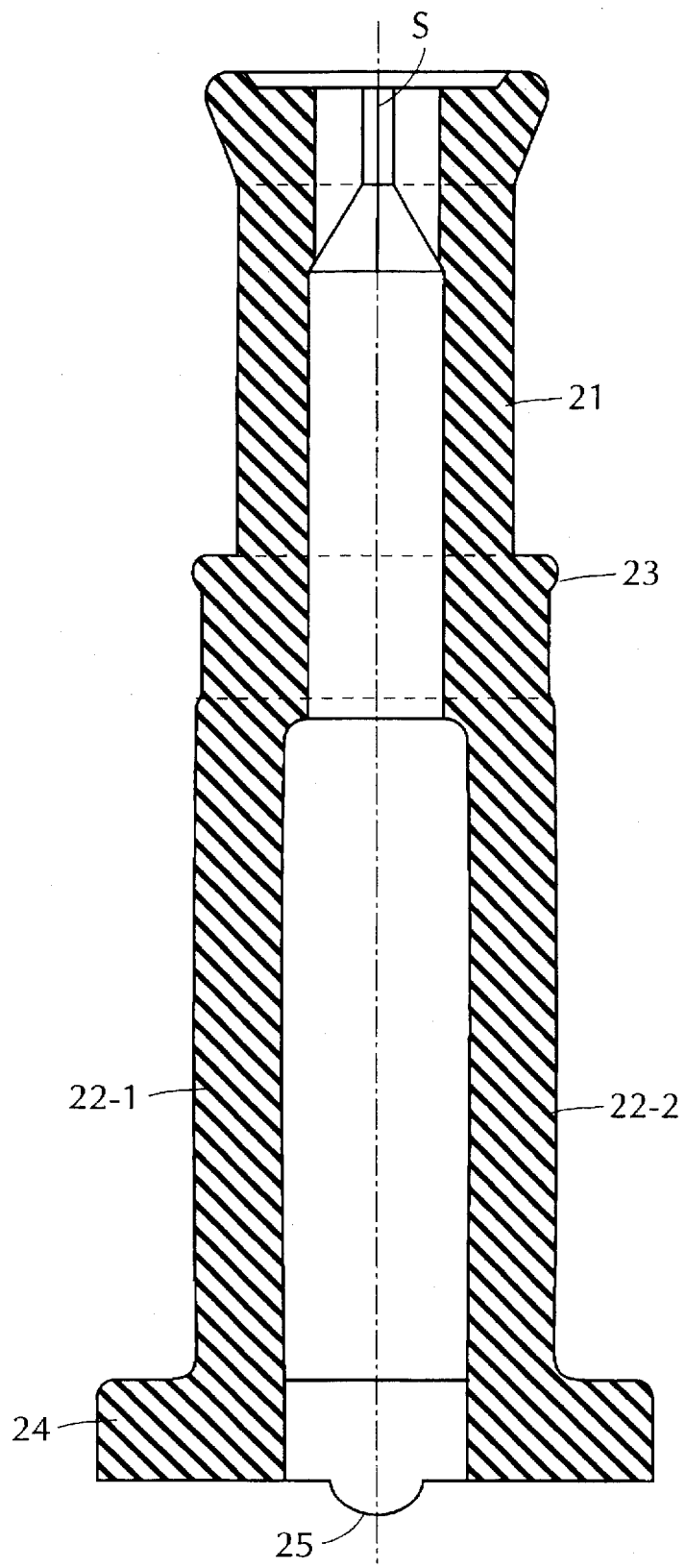
FIG. 5C is an enlarged sectional view of the flow-control plug of FIG. 5B in its "pre-installation" condition.
Figure 5D:
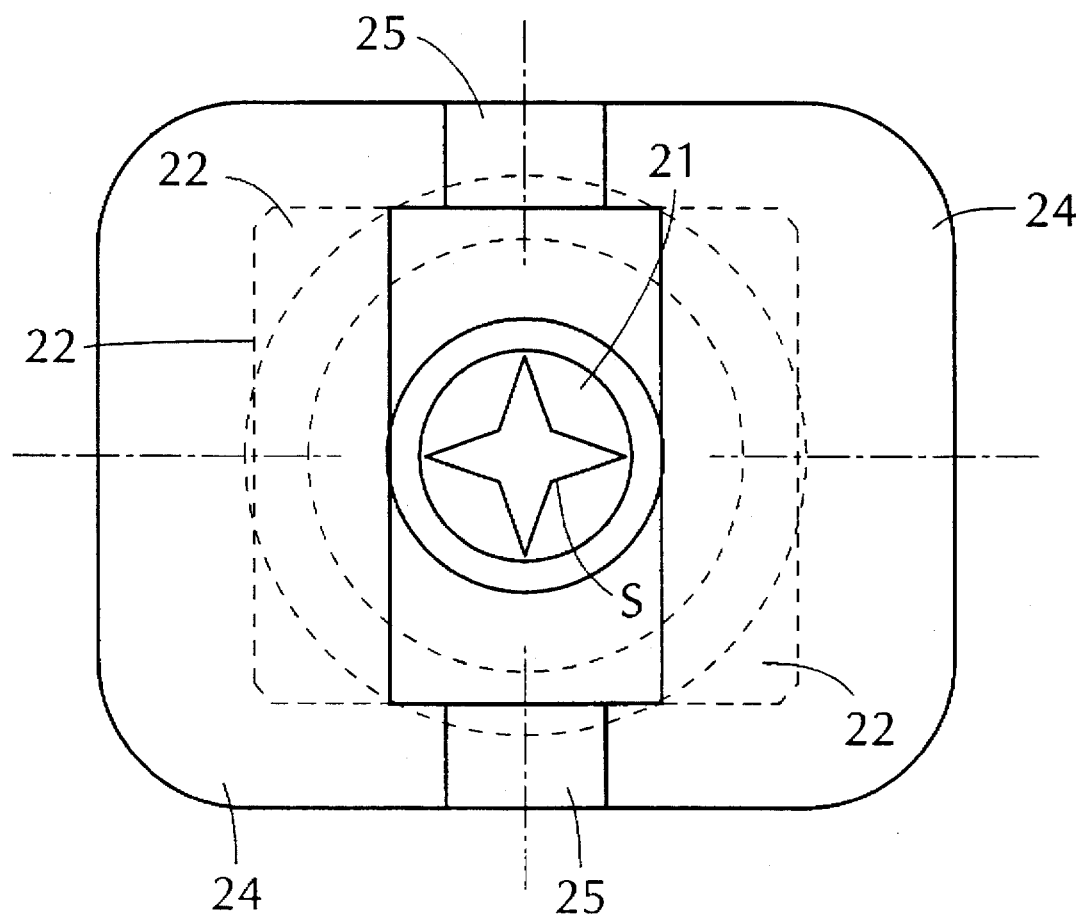
FIG. 5D is a bottom view of the flow-control plug of FIGS. 5B and 5C.

FIG. 5A is a scale view of one side of a flow-control plug 20 for the valve 10 of FIG. 1A, and FIG. 5B is an enlarged view of the flow-control plug of FIG. 5A in its "pre-installation" condition, while FIG. 5C is an enlarged sectional view of the flow-control plug of FIG. 5B in its "pre-installation" condition with a star-shaped slot S. FIG. 5D is a bottom view of the open, star-shaped slot S in the flow-control plugs of FIGS. 5B and 5C.

Figure 6A:
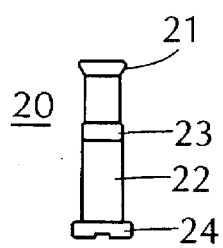
FIG. 6A is a scale view of the other side of the flow-control plug for the valve of FIG. 1A.
Figure 6B:
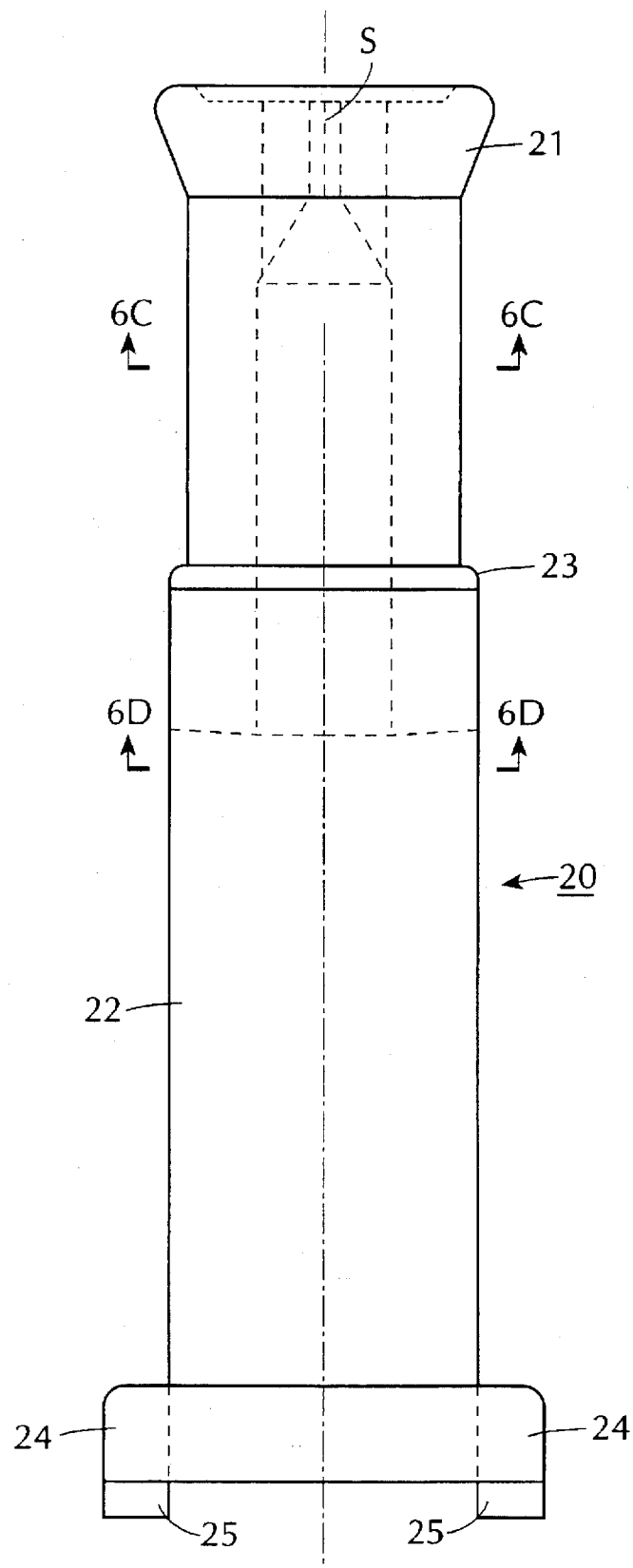
FIG. 6B is an enlarged view of the flow-control plug of FIG. 6A in its "pre-installation" condition.
Figure 6C:
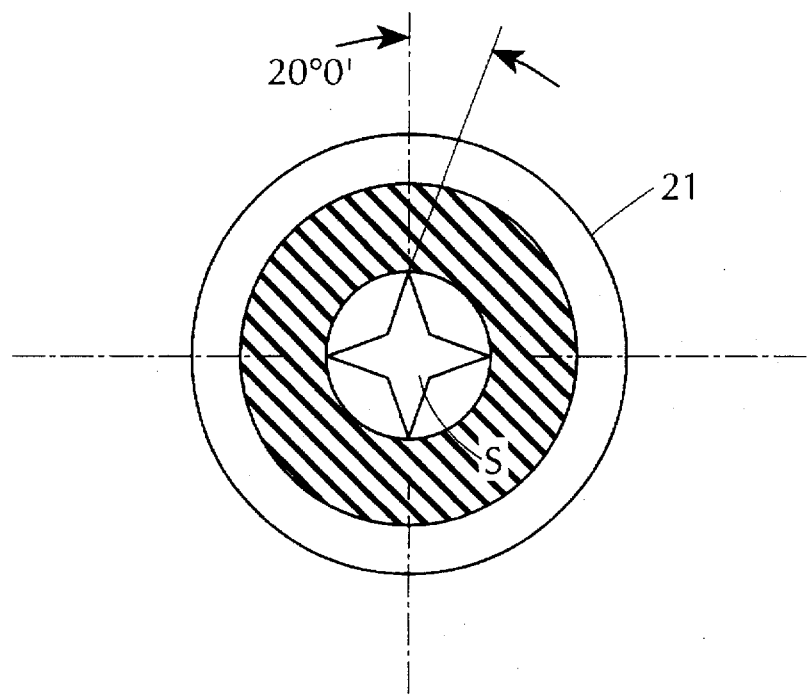
FIG. 6C is a sectional view of the flow-control plug of FIG. 6B in its "pre-operation" condition taken along the lines 6C—6C.
Figure 6D:
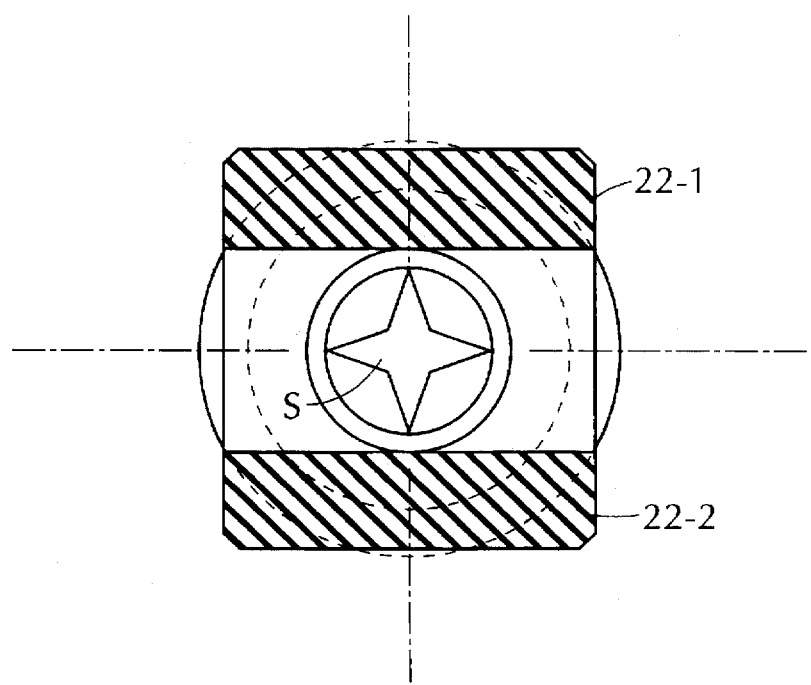
FIG. 6D is a sectional view of the flow-control plug of FIG. 6B taken along the lines 6D—6D.
Figure 6E:
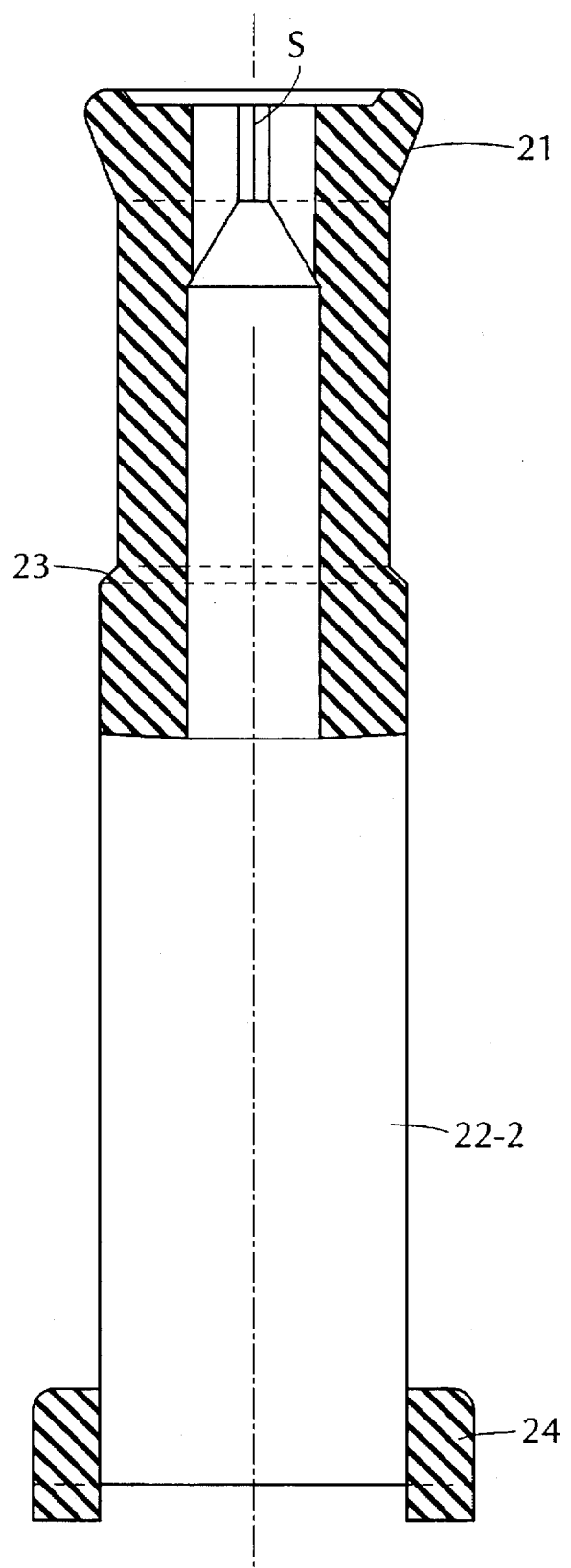
FIG. 6E is a sectional view of the flow-control plug of FIG. 6B.

FIG. 6A is a scale view of the other side of the flow-control plug for the valve of FIG. 1A, and FIG. 6B is an enlarged view of the flow-control plug of FIG. 6A showing the open star-shaped slot S in phantom in its "pre-installation" condition. FIG. 6C is a sectional view of the flow-control plug of FIG. 6B in its "pre-installation" condition taken along the lines 6C—6C showing the open star-shaped slot S, and FIG. 6D is a sectional view of the flow-control plug of FIG. 6B taken along the lines 6D—6D, while FIG. 6E is a sectional view of the flow-control plug of FIG. 6B.

Figure 7A:
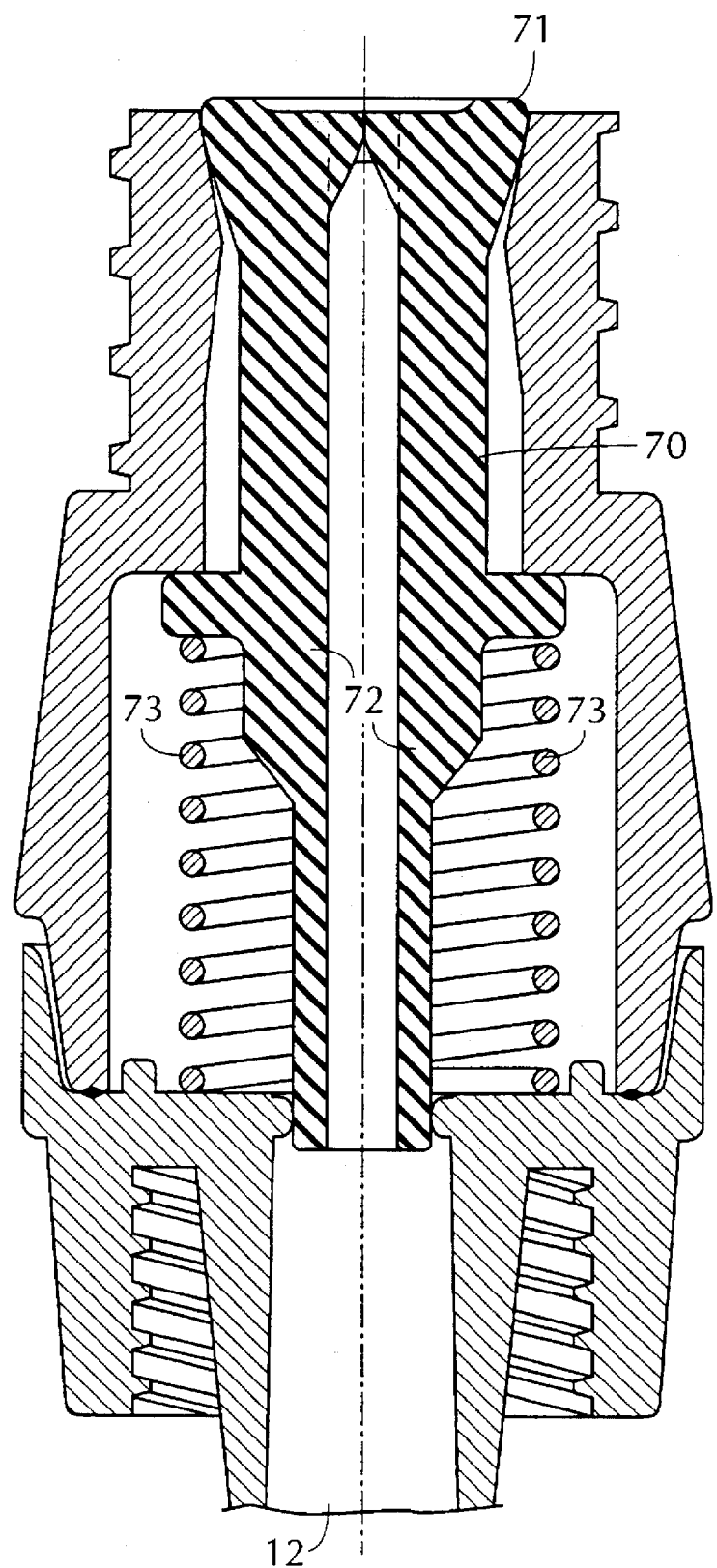
FIG. 7A is a cross-sectional view of an alternative flow-control valve in accordance with the invention.
Figure 7B:
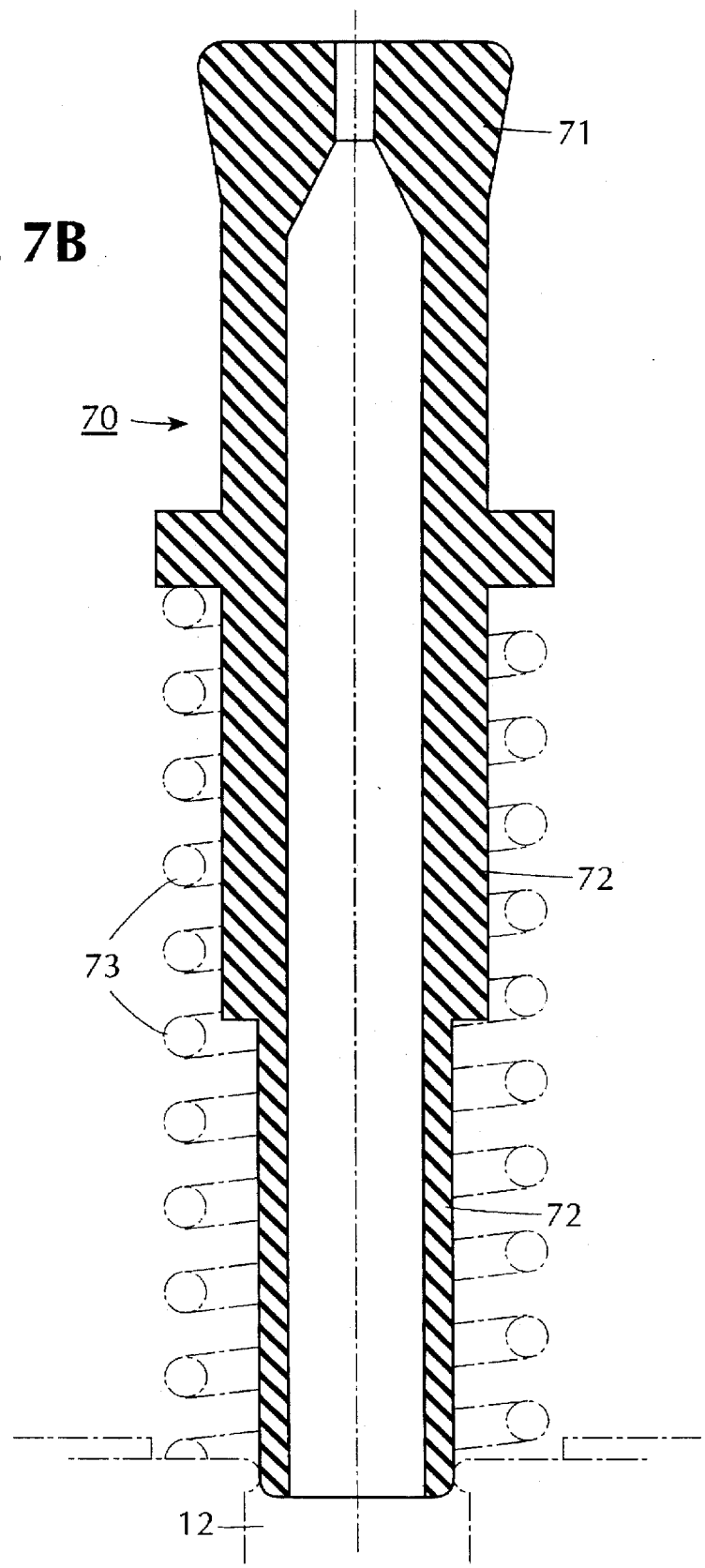
FIG. 7B is an enlargement showing details for the spring-loaded plug of FIG. 7A.
Figure 8A:
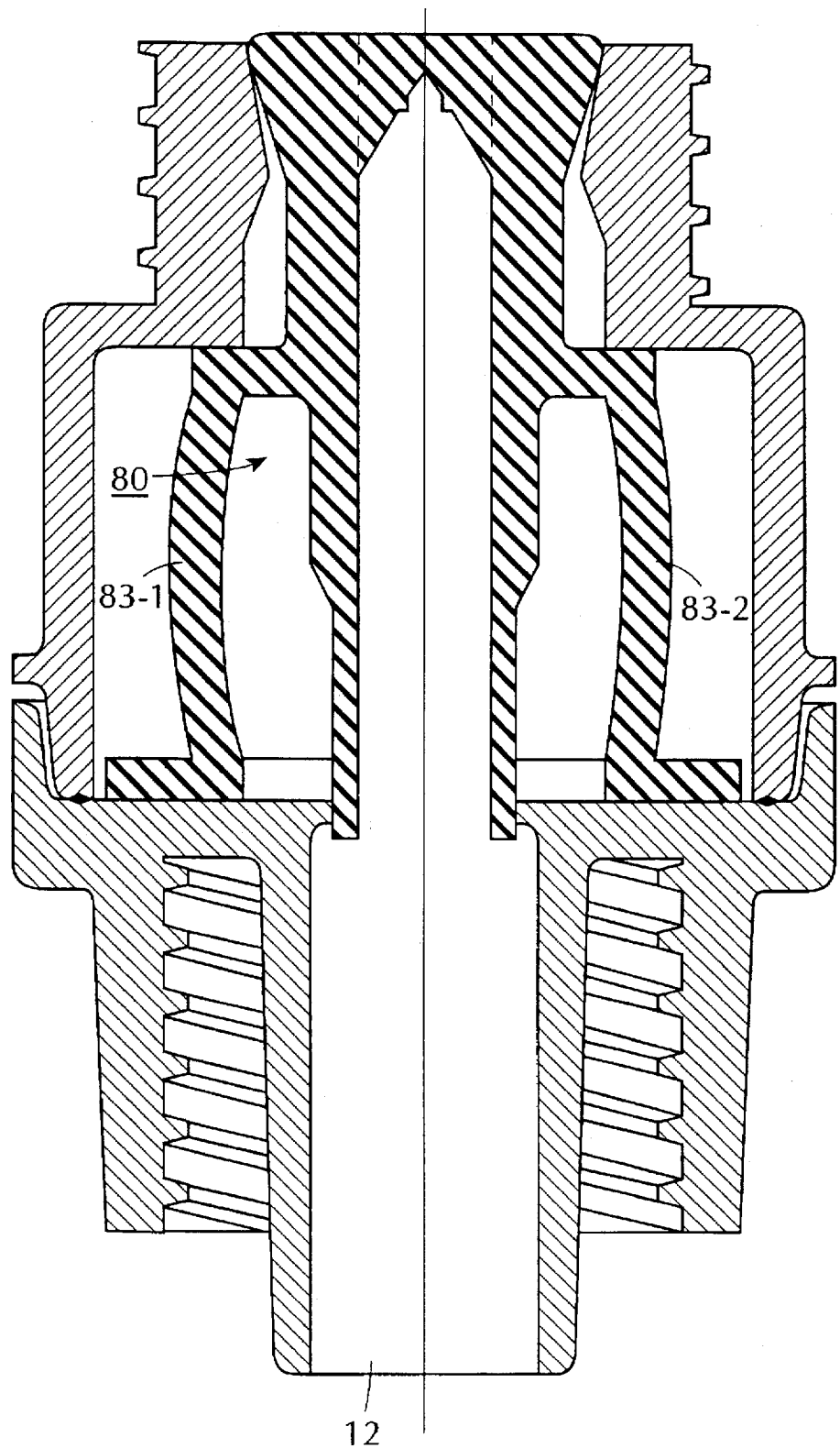
FIG. 8A is a cross-sectional view of an alternative to the flow-control valve of FIG. 7A in accordance with the invention.
Figure 8B:
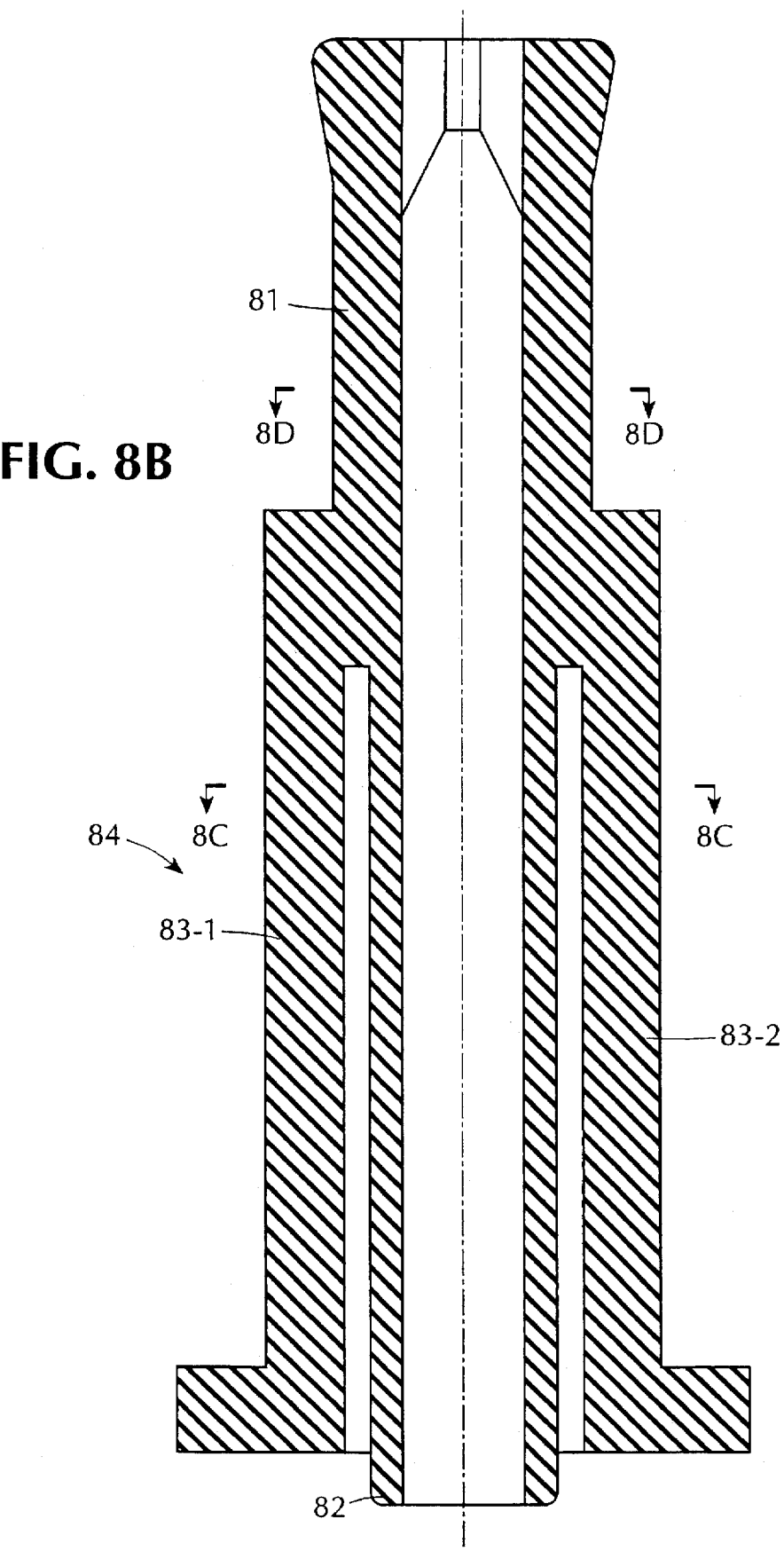
FIG. 8B is an enlargement showing alternative details for the plug of FIG. 8A.
Figure 8C:
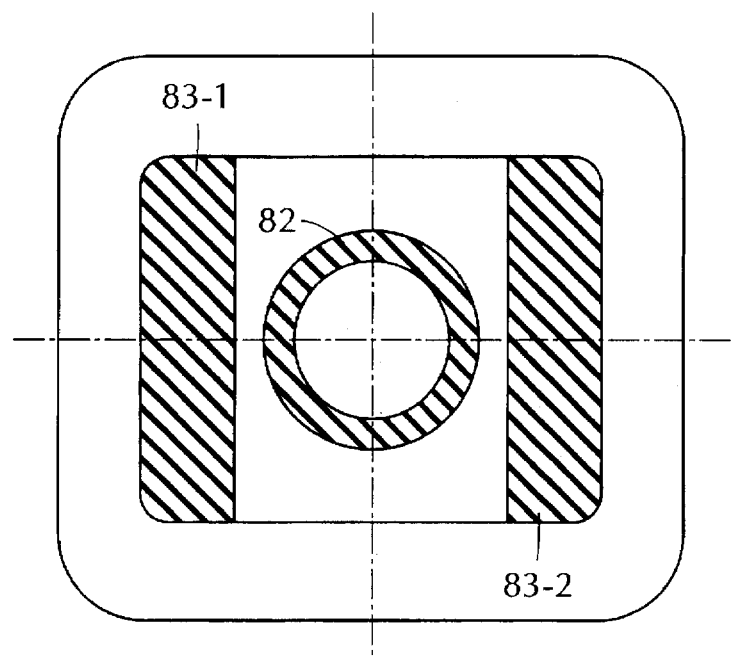
FIG. 8C is a cross-sectional view of the plug of FIG. 8B taken along the lines B—B.
Figure 8D:
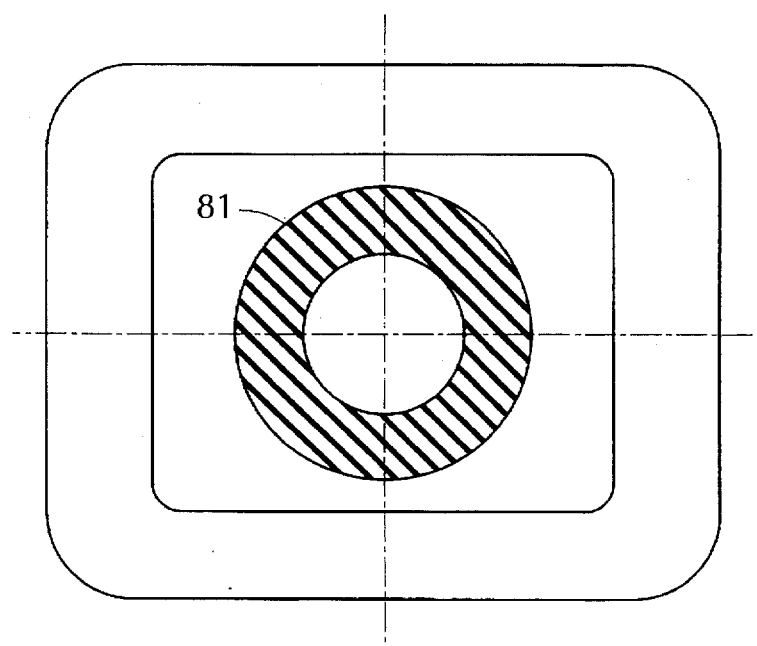
FIG. 8D is a cross-sectional view of the plug of FIG. 8B taken along the lines 8D—8D.

An alternative flow control plug 70 in accordance with the invention is shown in FIG. 7A. The plug 70 is used with the same general outer structure as the device 10 of FIG. 1A. However the plug 70 has a closed channel 72 which extends from a head 71 (like the head 11 of FIG. 1A) and is freely movable into the outlet 12 when the head is depressed. In order to restore the plug to its equilibrium condition when pressure to the head is removed, the plug 70 includes a spring 73, which is metallic in FIGS. 7A and 7B. A non-metallic, e.g. plastic spring, comprising resilient legs 83-1 and 83-2, is shown in FIG. 8A. FIG. 8B shows an alternative-shaped plug 84 with a head 81 and a spring portion 84, also comprising resilient legs 83-1 and 83-2. It will be appreciated that a metallic spring does not cause contamination in the embodiment of FIGS. 7A and 7B because the closed channel prevents fluid contact with the spring.

Figure 9A:
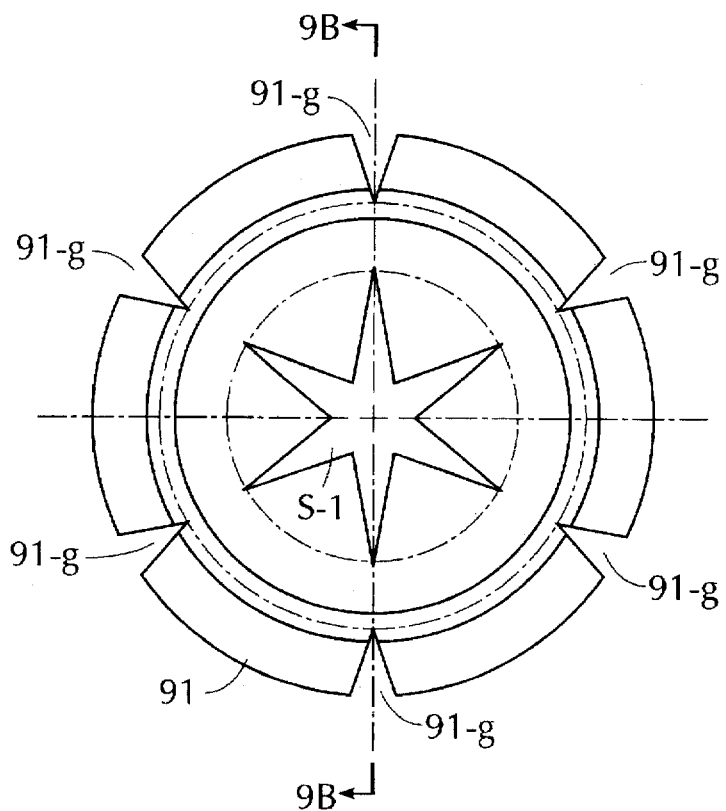
FIG. 9A is an enlarged end view of an alternative tip for the plugs of FIGS. 1A through 8D.
Figure 9B:
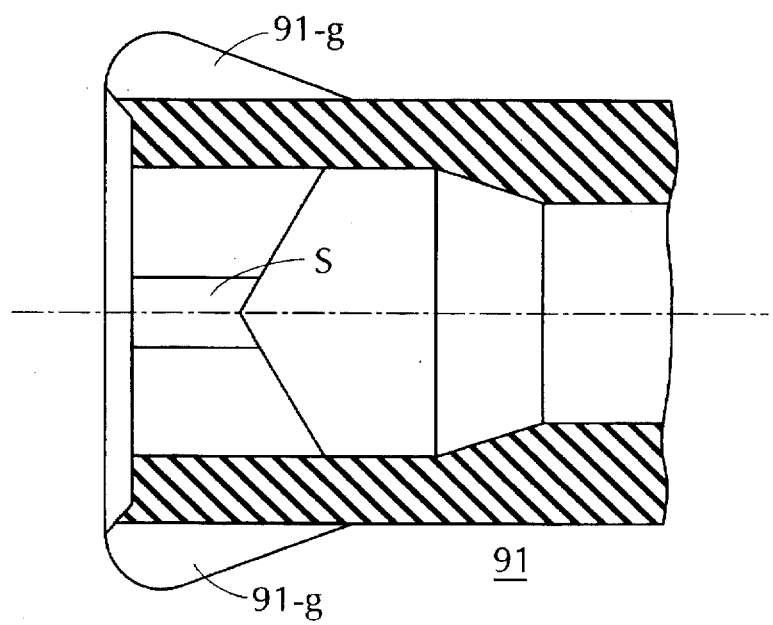
FIG. 9B is a partial cross-section of the tip of FIG. 9A taken along the lines 9B—9B.
Figure 10A:
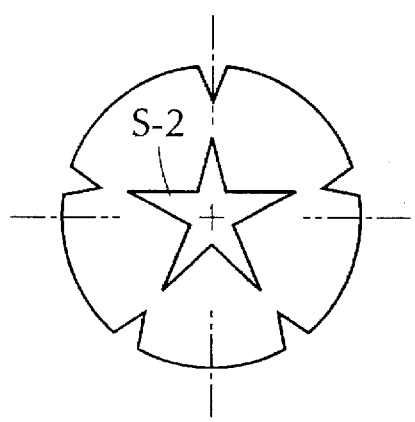
Figure 10B:
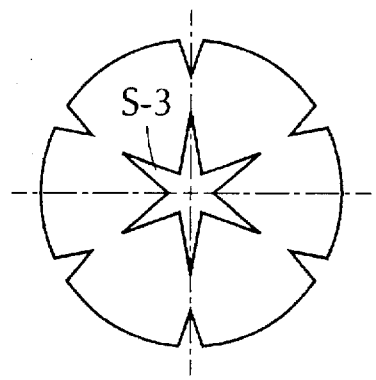
Figure 10C:
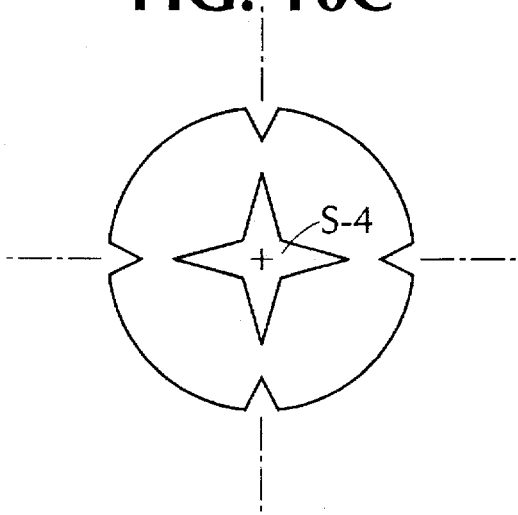
Figure 10C:
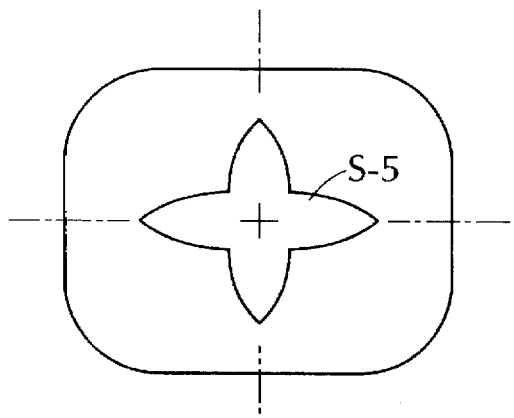
Figure 10E:
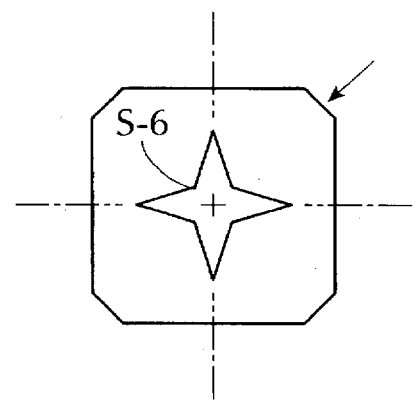

In order to facilitate the sealing of the head 11 it desirably takes the modified form 91 shown in FIGS. 9A and 9B with side grooves 91-g. In addition the open, star-shaped slot S-1 of FIG. 9A is six-pointed, with segments to facilitate complete closure of the slot S-1 when the valve is sealed. Still other forms for the slot S are illustrated by the open, star-shaped slots S-2 through S-6 of FIGS. 10A through 10E. In addition the heads of FIGS. 10B and 10E are square, as shown in FIG. 10E, or rectangular, as shown in FIG. 10D. The ring 93 defined by the phantom lines 95, 96 indicates the region of contact between an externally activating male Luer and the top surface of the head 91.

Figure 11A:
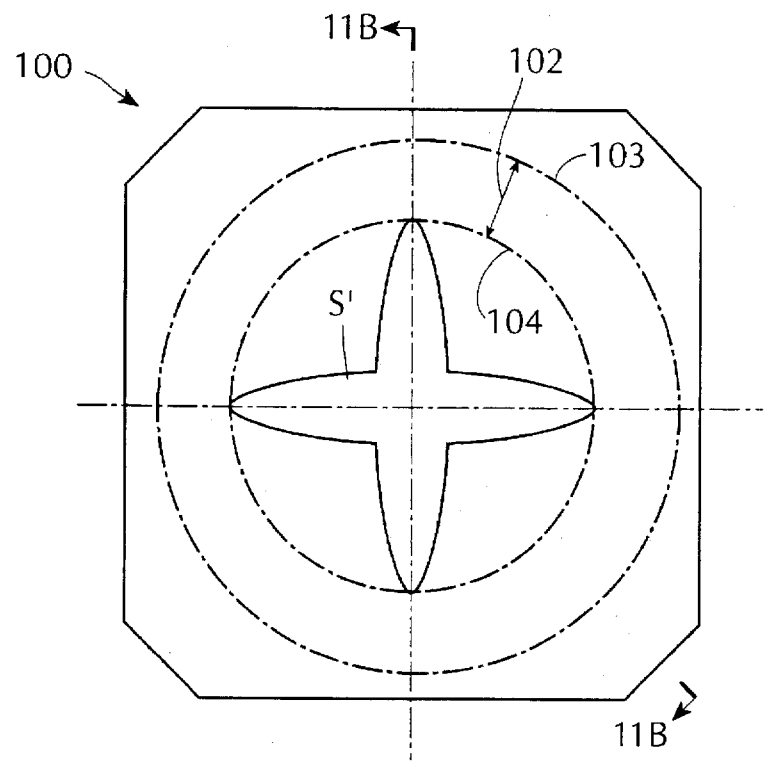
FIG. 11A is an enlarged end view of an alternative tip for the plugs of FIGS. 1A through 8D.
Figure 11B:
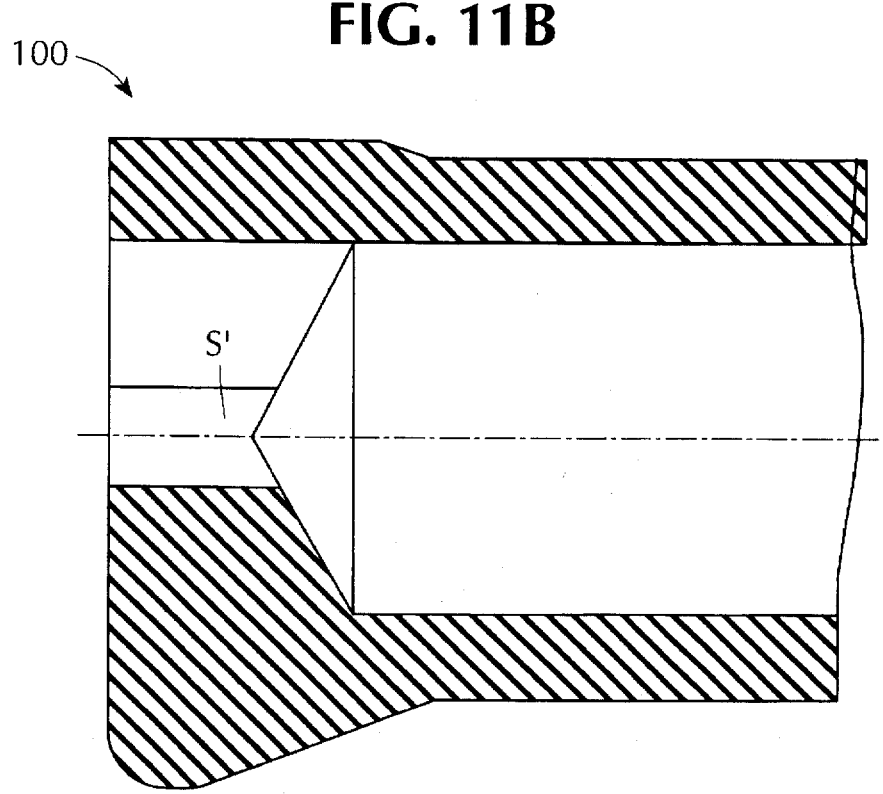
FIG. 11B is a partial cross-section of the tip of FIG. 11A taken along the lines 11B—11B.

A square plug similar to that of FIG. 10, except for having open, star-shaped slot S' with arcuate sides is shown in FIG. 11A, and is illustrated in FIG. 11B, in partial cross-section taken along the lines 11B—11B in FIG. 11A. This form of plug achieves the same kind of sealing effect that is achieved by use of the grooves 91-g in FIGS. 9A and 9B. The ring 102 defined by phantom lines 103, 104 indicates the region of contact between the externally activating male Luer and the top surface of the square plug 100.

It will be understood that the foregoing embodiments are illustrative only and that modifications and adaptations of the invention may be made without departing from its spirit and scope as defined in the appended claims.

What is claimed:

1. A flow control device comprising:
   an inlet for the flow of fluid;
   an outlet connected to said inlet and disposed with respect thereto to serve as a conduit for flow from said inlet; and
   slidable movable means having a normally open slotted and compressible head for sealing said inlet, said inlet closing the slot from a completely open to a completely closed condition when said head is within said inlet, and a flexible body including a channel extending to said outlet for permitting flow through said head to said outlet when said inlet is unsealed.

2. A flow control device in accordance with claim 1 wherein said inlet extends to a tapered bore which is spaced from said movable means, and the slot of said head is opened when said head is moved into said tapered bore.

3. A flow control device in accordance with claim 2 wherein said tapered bore extends to a second bore within which said flexible body is expandable outwardly with respect to the axis of said outlet.

4. A flow control device in accordance with claim 3 wherein said flexible body is spaced from said second bore to permit expansion and contraction during the opening and closing of said slot.

5. A flow control device in accordance with claim 1 further including means for permitting the activation of said movable means by a member external to the flow control device which does not penetrate the slot of said head, wherein said moveable means terminates in said head sealing said inlet and said head can be moved from said inlet by the external member.

6. A flow control device in accordance with claim 1 wherein an inner flow passage extends continuously from said slot to said outlet.

7. A flow control device in accordance with claim 1 wherein the slot of said head is in the form of a multi-sided geometric figure with opened segments when said head is in a non-sealing position.

8. A flow control device in accordance with claim 1 wherein said head has a depressed surface that is sealingly complementary to and non-penetrable by the tip of a Luer taper at the entrance to said inlet.

9. A flow control device as defined in claim 1 wherein said inner flow passage extends into said outlet and is movable therein from an equilibrium position, whereby the removal of a force causing said inner flow passage to move into said outlet opening the slot causes the inner flow passage to return to its equilibrium position closing the slot.

10. A flow control device in accordance with claim 1, wherein said head comprises an outer peripheral surface having grooves extending in the direction of movement of said head.

11. A method of controlling fluid flow which comprises the steps of:
    (1) sealing an inlet by a normally open slotted flexible stopper which compresses into said inlet, said inlet closing the slot of said stopper; and
    (2) slidably depressing said stopper to open the slot and permit the flow of fluid therethrough.

12. The method of claim 11 further including the step of depressing said stopper by applying the tip of a Luer taper thereto without engaging said slot.

13. The method of claim 11 further including the step of depressing said stopper to cause the expansion thereof and open the slot therein to permit the passage of fluid therethrough.

14. The method of controlling fluid flow in accordance with claim 11 wherein the depression of said stopper spontaneously opens the slot to permit the flow of fluid therethrough.

15. A flow control device comprising:
    an inlet for the flow of fluid;
    an outlet;
    a conduit connecting said inlet to said outlet to enable fluid flow from said inlet to said outlet;
    a normally open slotted and compressible head movably disposed between said inlet and said outlet, wherein said inlet closes the slot when said head is within said inlet, sealing said inlet, and said slot is opened when said head is moved out of said inlet, allowing fluid to flow through said conduit.

16. A flow control device in accordance with claim 15, wherein a portion of said conduit proximate said inlet is a tapered bore, and the slot is opened when said head is moved into said tapered bore.

17. A flow control device in accordance with claim 15, wherein said head has a depressed surface that is sealingly complementary to and non-penetrable by the tip of a Luer taper at the entrance of said outlet.

18. A flow control device in accordance with claim 15, wherein said head comprises an outer peripheral surface having grooves extending in the direction of movement of said head.

19. A flow control device in accordance with claim 15, further comprising a valve body including said inlet and said outlet, said valve body having an exterior surface with at least one flat portion.

20. A flow control device in accordance with claim 16, further comprising a valve body including said inlet and said outlet, said valve body having an exterior surface with a rectangular cross-section.

* * * * *

UNITED STATES PATENT AND TRADEMARK OFFICE
CERTIFICATE OF CORRECTION

PATENT NO.    : 5,699,821
DATED         : December 23, 1997
INVENTOR(S)   : JOSEPH R. PARADIS It is certified that error appears in the above-identified patent and that said Letters Patent is hereby corrected as shown below:

Col. 4, line 46, "pre-operation" should read --pre-installation--.
Col. 4, line 62, "B-B" should read --8C-8C--.

Signed and Sealed this

Sixteenth Day of June, 1998

Attest:

BRUCE LEHMAN

Attesting Officer                Commissioner of Patents and Trademarks